United States Patent [19]

Hillard et al.

[11] 4,061,681

[45] Dec. 6, 1977

[54] METHOD FOR THE PREPARATION OF MONO- OR POLY [DIALKYL OR DICYCLOALKYLPHOSPHONYLMETHYL] AROMATIC CARBOCYCLIC COMPOUNDS

[75] Inventors: Ray Leonard Hillard; Norma Ann Weston, both of R.D. Annandale, N.J.

[73] Assignee: American Cyanamid Company, Stamford, Conn.

[21] Appl. No.: 731,288

[22] Filed: Oct. 12, 1976

[51] Int. Cl.² .............................................. C07F 9/53
[52] U.S. Cl. .............................................. 260/606.5 P
[58] Field of Search .................................. 260/606.5 P

[56] References Cited

U.S. PATENT DOCUMENTS

| | | | |
|---|---|---|---|
| 3,117,165 | 1/1964 | Epstein | 260/606.5 P |
| 3,145,234 | 8/1964 | Buckler et al. | 260/606.5 P |
| 3,660,495 | 5/1972 | Lin | 260/606.5 P |
| 3,745,191 | 7/1973 | Daigle et al. | 260/606.5 P |
| 3,746,758 | 7/1973 | Spivack | 260/606.5 P |
| 3,895,074 | 7/1975 | Mrowca | 260/606.5 P |

*Primary Examiner*—Helen M. S. Sneed
*Attorney, Agent, or Firm*—Frank M. Van Riet

[57] ABSTRACT

Mono- and poly [dialkyl or dicycloalkylphosphonylmethyl] aromatic carbocyclic compounds are prepared by reacting an appropriately substituted secondary phosphine with formaldehyde, reacting the resultant dialkyl or dicyclohydroxymethylphosphine with an appropriately substituted halomethyl aromatic compound and oxidizing the resultant secondary phosphine.

12 Claims, No Drawings

METHOD FOR THE PREPARATION OF MONO- OR POLY [DIALKYL OR DICYCLOALKYLPHOSPHONYLMETHYL] AROMATIC CARBOCYCLIC COMPOUNDS

BACKGROUND OF THE INVENTION

Poly[di(2-cyanoethyl)phosphonylmethyl]aromatic compounds are known flame-retardant compounds for thermoplastic polymers. They are described by Hoffman in U.S. Pat. Nos. 3,835,119, 3,895,048, and 3,917,560. The preparation of the compounds is described in U.S. Pat. No. 3,895,048, whereby various (2-cyanoethyl)phosphine oxides are reacted with an appropriately substituted halomethyl aromatic compounds, for example, 1,4-bis-(chloromethyl) benzene.

Although that method is very effective for the preparation of poly[di(2-cyanoethyl)phosphonylmethyl]-aromatic compounds, problems are frequently encountered when attempts are made to utilize the method for the preparation of their mono- or poly[dialkylphosphonylmethyl]aromatic analogs. Thus, in many instances the appropriate phosphine oxide either is unavailable or the reaction to prepare the phosphine oxide does not proceed as expected. For instance, attempts to prepare bis (cyclohexyl)phosphine oxide by oxidation of the corresponding phosphine lead to the formation of the phosphinic acid.

There is a need, therefore, for a generally applicable method for the preparation of mono- or poly[dialkyl- or dicycloalkylphosphonylmethyl]aromatic carbocyclic compounds.

SUMMARY OF THE INVENTION

We have now discovered that these mono- or poly[-dialkyl or dicycloalkylphosphonylmethyl] aromatic carbocyclic compounds may be prepared according to a method whereby the appropriate secondary phosphine is first reacted with formaldehyde to form the corresponding hydroxymethyldialkylphosphine; the hydroxymethyldialkylphosphine is next reacted with the appropriate halomethyl aromatic compound to produce the corresponding mono- or poly-[dialkylphosphinomethyl]aromatic compound, which is then oxidized to the phosphonylmethyl compound.

Although we do not know the mechanism by which the above-described process produces the mono- or poly[dialkylphosphinomethyl]aromatic compound, it is believed an unstable intermediate is formed. While not wishing to be held to any specific theory, it is possible that the unstable intermediate readily decomposes to the desired product. The following is a postulated structure for said intermediate:

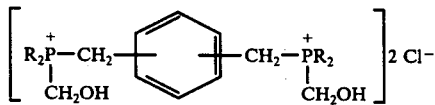

DESCRIPTION OF THE INVENTION INCLUDING PREFERRED EMBODIMENTS

As mentioned above, invention relates to a method for the preparation of mono- or poly[dialkyl- or dicycloalkylphosphonylmethyl]aromatic carbocyclic compounds. These compounds are useful as flame-retarding agents for thermoplastic polymers and may be represented by the formula:

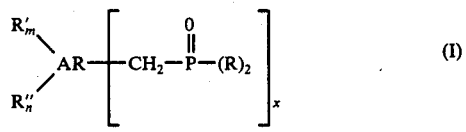

wherein R represents an alkyl radical containing from 1 to 8 carbon atoms or a cycloalkyl radical containing 5 or 6 carbon atoms in a ring, said ring optionally being further substituted with one or more lower alkyl ($C_1$–$C_4$) groups; $R^1$ and $R^2$ represent, individually, methyl, ethyl, or methoxy radicals; AR is benzene or naphthalene; and when AR is benzene, $m$ and $n$ are, individually, integers from 0 to 5, inclusive, and $x$ is an integer from 1 to 6, inclusive; when AR is naphthalene, $m$ and $n$ are, individually, integers from 0 to 3, inclusive, and $x$ is an integer from 1 to 4, inclusive.

Compounds prepared in accordance with the invention are more particularly represented by one of Formulae (II) or (III):

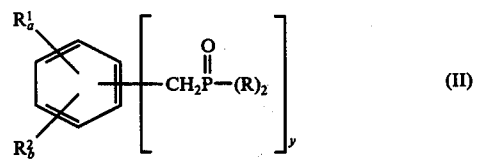

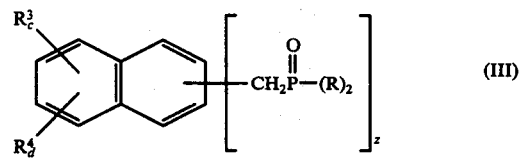

wherein R, $R^1$, $R^2$, $R^3$ and $R^4$ are as described above, $a$ and $b$, individually, represent integers from 0 to 5, inclusive; $c$ and $d$, individually, represent integers from 0 to 3, inclusive; Y represents an integer from 1 to 6, inclusive; and Z represents an integer from 1 to 4, inclusive.

Compounds falling within the scope of Formula II include:

1-[di(methyl)phosphonylmethyl]-2,4,6-trimethylbenzene;
1-[di(butyl)phosphonylmethyl]-2,4,6-trimethylbenzene;
1-[di(cyclohexyl)phosphonylmethyl]-2,4,6-trimethylbenzene;
1-[di(methyl)phosphonylmethyl]-4-methylbenzene;
1-[di-butyl)phosphonylmethyl]-4-methylbenzene;
1-[di(cyclohexyl)phosphonylmethyl]-4-methylbenzene;
1,4-phenylenebis[di(methyl)phosphonylmethyl];
1,4-phenylenebis[di(ethyl)phosphonylmethyl];
1,4-phenylenebis[di(n-propyl)phosphonylmethyl];
1,4-phenylenebis[di(isopropyl)phosphonylmethyl];
1,4-phenylenebis[di(n-butyl)phosphonylmethyl];
1,4-phenylenebis[di(n-octyl)phosphonylmethyl];
1,4-phenylenebis[di(cyclohexyl)phosphonylmethyl];
1,4-bis[di(methyl)phosphonylmethyl]-2,3,5,6-tetramethylbenzene;
1,4-bis[di(ethyl)phosphonylmethyl]-2,3,5,6-tetramethylbenzene;
1,4-bis[di(n-propyl)phosphonylmethyl]-2,3,5,6-tetramethylbenzene;

1,4-bis[di(isopropyl)phosphonylmethyl]-2,3,5,6-tetramethylbenzene;
1,4-bis[di(n-butyl)phosphonylmethyl]-2,3,5,6-tetramethylbenzene;
1,4bis[di(n-octyl)phosphonylmethyl]-2,3,5,6-tetramethylbenzene;
1,4-bis[di(cyclohexyl)phosphonylmethyl]-2,3,5,6-tetramethylbenzene;
2,4,6-tris[di(methyl)phosphonylmethyl]-mesitylene;
2,4,6-tris[di(ethyl)phosphonylmethyl]-mesitylene;
2,4,6-tris[di(n-propyl)phosphonylmethyl]-mesitylene;
2,4,6-tris[di(isopropyl)phosphonylmethyl]-mesitylene;
2,4,6-tris[di(n-butyl)phosphonylmethyl]-mesitylene;
2,4,6-tris[di(n-octyl)phosphonylmethyl]-mesitylene;
2,4,6-tris[di(cyclohexyl)phosphonylmethyl]-mesitylene;
1,2,4,5-tetrakis[di(methyl)phosphonylmethyl]-benzene;
1,2,4,5-tetrakis[di(ethyl)phosphonylmethyl]-benzene;
1,2,4,5-tetrakis[di(n-propyl)phosphonylmethyl]benzene;
1,2,4,5-tetrakis[di(isopropyl)phosphonylmethyl]benzene;
1,2,4,5-tetrakis[di(n-butyl)phosphonylmethyl]benzene;
1,2,4,5-tetrakis[di(n-octyl)phosphonylmethyl]benzene;
1,2,4,5-tetrakis[di(cyclohexyl)phosphonylmethyl]benzene;
2,4-bis[di(methyl)phosphonylmethyl]-1,3,5-trimethylbenzene;
2,4-bis[di(ethyl)phosphonylmethyl]-1,3,5-trimethylbenzene;
2,4-bis[di(n-propyl)phosphonylmethyl]-1,3,5-trimethylbenzene;
2,4-bis[di(isopropyl)phosphonylmethyl]-1,3,5-trimethylbenzene;
2,4-bis[di(n-butyl)phosphonylmethyl]-1,3,5-trimethylbenzene;
2,4-bis[di(n-octyl)phosphonylmethyl]-1,3,5-trimethylbenzene;
2,4-bis[di(cyclohexyl)phosphonylmethyl]-1,3,5-trimethylbenzene;
1,2,3,4,5,6hexakis[di(methyl)phosphonylmethyl]benzene;
1,2,3,4,5,6-hexakis[di(ethyl)phosphonylmethyl]benzene;
1,2,3,4,5,6-hexakis[di(n-propyl)phosphonylmethyl]benzene;
1,2,3,4,5,6-hexakis[di(n-butyl)phosphonylmethyl]benzene;
1,2,3,4,5,6hexakis[di(n-octyl)phosphonylmethyl]benzene;
1,2,3,4,5,6-hexakis[di(cyclohexyl)phosphonylmethyl]benzene and the like.

Compounds falling within the scope of Formula III include:
2-[di(methyl)phosphonylmethyl]naphthalene;
2-[di(ethyl)phosphonylmethyl]naphthalene;
1,5-bis[di(methyl)phosphonylmethyl]naphthalene;
1,5-bis[di(ethyl)phosphonylmethyl]naphthalene;
1,5-bis[di(n-propyl)phosphonylmethyl]naphthalene;
1,5-bis[di(isopropyl)phosphonylmethyl]naphthalene;
1,5-bis[di(n-butyl)phosphonylmethyl]naphthalene;
1,5-bis[di(n-octyl)phosphonylmethyl]naphthalene;
1,5-bis[di(cyclohexyl)phosphonylmethyl]naphthalene;
2,6-bis[di(methyl)phosphonylmethyl]naphthalene;
2,6-bis[di(ethyl)phosphonylmethyl]naphthalene;
2,6-bis[di(n-propyl)phosphonylmethyl]naphthalene;
2,6-bis[di(isopropyl)phosphonylmethyl]naphthalene;
2,6-bis[di(n-butyl)phosphonylmethyl]naphthalene;
2,6-bis[di(n-octyl)phosphonylmethyl]naphthalene;
2,6bis[di(cyclohexyl)phosphonylmethyl]naphthalene;
2,3,6-tris[di(methyl)phosphonylmethyl]naphthalene;
2,3,6-tris[di(ethyl)phosphonylmethyl]naphthalene;
2,3,6-tris[di(n-propyl)phosphonylmethyl]naphthalene;
2,3,6-tris[di(isopropyl)phosphonylmethyl]-naphthalene;
2,3,6tris[di(n-butyl)phosphonylmethyl]-naphthalene;
2,3,6tris[di(n-cotyl)phosphonylmethyl]-naphthalene;
2,3,6tris[di(cyclohexyl)phosphonylmethyl]-naphthalene;
1,6-bis[di(n-propyl)phosphonylmethyl]-2-methoxynaphthalene;
1,6-bis[di(methyl)phosphonylmethyl]-2-methoxynaphthalene;
1,6-bis[di(ethyl)phosphonylmethyl]-2-methoxynaphthalene;
1,6bis[di(isopropyl)phosphonylmethyl]-2-methoxynaphthalene;
1,6-bis[di(n-butyl)phosphonylmethyl]-2-methoxynaphthalene;
1,6-bis[di(n-octyl)phosphonylmethyl]-2-methoxynaphthalene;
1,6-bis[di(cyclohexyl)phosphonylmethyl]-2-methoxynaphthalene;
2,3,6,7-tetrakis[di(methyl)phosphonylmethyl]-naphthalene;
2,3,6,7-tetrakis[di(ethyl)phosphonylmethyl]-naphthalene;
2,3,6,7-tetrakis[di(n-octyl)phosphonylmethyl]-naphthalene;
2,3,6,7-tetrakis[di(cyclohexyl)phosphonylmethyl]-naphthalene; and the like.

The secondary dialkyl- or dicycloalkylphosphines used in the first step of the present invention may be prepared by the free radical addition of phosphine to an olefin, according to procedures described by Stiles et al., U.S. Pat. No. 2,803,597. Dimethylphosphine is prepared according to the procedure of Inorganic Syntheses II, 126 (1969).

The halomethylated aromatic compounds used in the second step of the present process may be conveniently prepared by reacting the corresponding benzene or naphthalene with formaldehye and a hydrogen halide, e.g. hydrogen chloride, hydrogen bromide, etc., according to known procedures, such as those disclosed in U.S. Pat. Nos. 2,945,894, 2,951,100, 2,973,391, and 3,069,480. Alternatively, chlorination or bromination of the methyl groups of the appropriate methylbenzene or methylnaphthalene in the presence of a suitable catalyst may be used; see U.S. Pat. Nos. 2,926,202 and 2,956,084.

In accordance with the process of the present invention, the compounds of Formula I, above, are prepared by first reacting the appropriately substituted phosphine with formaldehye to form the corresponding hydroxymethylated tertiary phosphine:

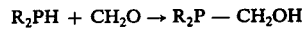

$$R_2PH + CH_2O \rightarrow R_2P-CH_2OH$$

wherein R is as defined hereinabove.

This reaction is readily accomplished by the addition of aqueous formaldehyde or paraformaldehyde to a solution of the phosphine in a low boiling, water miscible organic solvent, such as isopropanol, or an aqueous solution thereof, at moderate temperatures, i.e. 30° to 70° C, until the reaction is completed. Reaction progress is conveniently determined by monitoring an infrared spectrum of the reaction mixture until there is no longer evidence of a —PH band. Suitable reaction solvents in addition to isopropanol include water, methanol, dimethylformamide, acetonitrile and dioxane. The solvent is preferably one in which both the secondary phosphine and the product are soluble.

The appropriate halomethylated aromatic compound is then added to the solution of the hydroxymethylated tertiary phosphine at a temperature of about 25°–30° C. This reaction is normally mildly exothermic. The halomethylated aromatic compound may be added neat or as a solution. If necessary, the reaction mixture may be heated to a moderate temperature e.g. up to about 80° C for a period of time sufficient to complete the reaction. The mole ratio of tertiary phosphine to haloaromatic compound is at least that which is stoichiometrically required; preferably the hydroxymethylated tertiary phosphine is used in excess.

The product obtained, i.e. the phosphine precursor to the phosphine oxides represented by Formulae II and III, is then dissolved in a suitable solvent, such as acetic acid, and oxidized to the corresponding phosphine oxide. Many of these precursor compounds oxidize readily in air without the extraneous addition of an oxidant. The self-oxidation may occur during or after reaction of the halomethyl aromatic compound with the hydroxymethylated tertiary phosphine. Where the precursor compounds do not self-oxidize, they may be oxidized by the addition of an oxidant. Ordinarily aqueous hydrogen peroxide is used as the oxidant. The amount of oxidant used is in excess of that stoichiometrically required to oxidize each tertiary phosphine group in the molecule to the phosphine oxide. Excess oxidant is readily destroyed by the addition of manganese dioxide and warming the reaction mixture until evolution of oxygen ceases.

While acetic acid is a useful solvent for the oxidation reaction, other solvents such as water and cyclohexane may also be used.

Oxidants other than hydrogen peroxide which may be used include air, oxygen and the like.

The products produced by the process of the instant invention range from oils to solids. They may be isolated from the reaction mixture and purified by conventional means.

The following examples are set forth for purpose of illustration only and are not to be construed as limitations on the present invention except as set forth in the appended claims. All parts and percentages are by weight unless otherwise specified.

EXAMPLE 1

Preparation of 1,4-Bis[di(n-propyl)phosphonylmethyl]2,3,5,6-tetramethylbenzene

A. To a solution of 47.2 parts of di-n-propylphosphine in 100 ml. isopropanol are rapidly added 33.0 parts of 38% aqueous formaldehyde. The solution temperature slowly increases to about 40° C. When all the formaldehyde is added, the solution is stirred at 45°–50° C for about 3 hours. An infrared spectrum of the solution shows the absence of a —P-H band, indicating complete reaction to di-n-propylhydroxymethylphosphine.

B. To the above solution of di-n-propylhydroxymethylphosphine at room temperature is added 23.1 parts of 1,4-bis(chloromethyl)-2,3,5,6-tetramethylbenzene. The temperature of the solution slowly rises to about 35° C. The solution is heated to 45°–50° C for about 3 hours, cooled to room temperature and the solid product filtered and washed with water.

C. The resultant filter cake is then dissolved in about 200 ml. acetic acid and 23.0 parts of 30% aqueous hydrogen peroxide added dropwise at room temperature with rapid agitation. When all the hydrogen peroxide is added, the solution is heated to 50° C for about 30 minutes. Excess hydrogen peroxide is destroyed by the addition of manganese dioxide, carbon is added, and the reaction mixture is heated at steam bath temperature until oxygen evolution ceases. The mixture is then filtered and the clear yellow filtrate evaporated to give a yellow oil. The oil is drowned in water, whereupon a white crystalline solid precipitates. The precipitate is filtered, washed with water and dried. There are obtained 17 grams of the titled product which is recrystallized from isopropanol-water; m.p. 225°–227° C.

EXAMPLE 2

Preparation of 1,4-Bis[di(cyclohexyl)phosphonylmethyl]2,3,5,6-tetramethylbenzene Following the procedure of Example 1, 85.0 parts of dicyclohexyl phosphine in 200 ml. isopropanol is reacted with 33.0 parts of 38% aqueous formaldehyde to give a solution to which is added 23.1 parts of 1,4-bis(chloromethyl)-2,3,5,6-tetramethylbenzene. The resulting solid product is dissolved in 200 ml. acetic acid and 23.0 parts of 30% hydrogen peroxide are added. Following the oxidation step as in Example 1, the solution is stripped to give an oil, which is triturated with water, the water decanted, and the residue dissolved in methanol. The methanol solution is drowned in water and the solid filtered and dried; yield is 25 parts, m.p. 280°–283° C. The solid is recrystallized from 50/50-isopropanol/water to give the titled crystalline product; m.p. 283°–286° C.

EXAMPLE 3

Preparation of 1,4-Phenylenebis[bis(n-butyl)phosphonylmethylene]

The procedure of Example 1 is followed except that di-n-butylphosphine is used instead of di-n-propylphosphine and α,α', -dichloro-p-xylene is used instead of 1,4bis(chloromethyl)-2,3,5,6-tetramethylbenzene. The titled compound is recovered.

EXAMPLE 4

Preparation of 2,4,6-Tris[di(n-propyl)phosphonylmethyl]mesitylene

The procedure of Example 1 is followed except that 0.6 mole of dipropylphosphine is reacted with 0.1 mole of 2,4,6-tris(chloromethyl)mesitylene instead of 1,4-bis(chloromethyl)-2,3,5,6-tetramethylbenzene, and 0.3 mole of hydrogen peroxide is used instead of 0.2 mole. Again, the titled compound is produced.

EXAMPLE 5

Preparation of 1,2,4,5-Tetrakis[di(n-octyl)phosphonylmethyl]benzene

The procedure of Example 1 is followed except that 0.8 mole di-n-octylphosphine is used instead of 0.4 mole of di-n-propylphosphine; 1,2,4,5-tetrakis(chloromethyl)benzene is used instead of 1,4-bis(chloromethyl)-2,3,5,6-tetramethylbenzene; and 0.4 mole of hydrogen peroxide is used instead of 0.2 mole. Recrystallization from isopropanol-water results in the recovery of the titled compound.

EXAMPLE 6
Preparation of 2,3,6-Tris[di(cyclohexyl)phosphonylmethyl]naphthalene The procedure of Example 1 is followed except that 0.6 mole of dicyclohexylphosphine is used instead of 0.4 mole of di-n-propylphosphine; 2,3,6-tris(chloromethyl) naphthalene is used instead of 1,4-bis(chloromethyl)-2,3,5,6-tetramethylbenzene; and 0.3 mole of hydrogen peroxide is used instead of 0.2 mole. The titled compound is recovered after recrystallization.

EXAMPLE 7
Preparation of 1-[Di(cyclohexyl)phosphonylmethyl]-2,4,6-trimethylbenzene To a solution of 40.9 parts of 98% dicyclohexylphosphine in 50 ml. isopropanol was added 15.8 parts of 38% formaldehyde. Five minutes after the addition, a sample of the reaction mixture shows the absence of a

bond in the infrared spectrum. The reaction mixture is stirred for 60 minutes and 16.9 parts of α²-chloroisodurene are added thereto. The temperature increased from 26° C to 56° C, and the reaction mixture is then stirred for 22 hours at 55° C. When cooled to room temperature, the reaction mixture is diluted with water and extracted with benzene. The benzene extracts are combined, washed with water and dried. Evaporation of the benzene gives 32.4 parts of a yellow oil. Trituration of the oil with petroleum ether gives a white solid, m.p. 139°–143° C which is recrystallized from boiling hexane to give a white solid, m.p. 142°–145° C. The product is confirmed by elemental analysis as the titled compound, oxidation occurring spontaneously.

EXAMPLE 8
Preparation of 1,6-bis[di(cyclohexyl)phosphonylmethyl]-2-methoxynaphthalene The procedure of Example 7 is again followed except that the α²-chloroisodurene is replaced by 1,6-bis(chloromethyl)-2-methoxynaphthalene. The titled compound is recovered from boiling hexane in good yield.

EXAMPLE 9
Preparation of 1,4bis[di(cyclohexyl)phosphonylmethyl]-2,3,5,6-tetraethylbenzene Following the procedure of Example 2 except that the 1,4-bis(chloromethyl)-2,3,5,6-tetramethylbenzene is replaced by 1,4-bis(chloromethyl)-2,3,5,6-tetraethylbenzene, the titled compound is produced as a crystalline solid.

We claim:

1. A method for the preparation of a phosphine oxide represented by the formula:

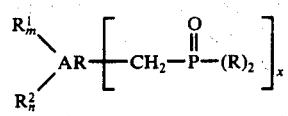

wherein R represents an alkyl radical containing from 1 to 8 carbon atoms or a cycloalkyl radical containing 5 or 6 carbon atoms in a ring, said ring optionally being further substituted with one or more lower alkyl ($C_1$ to $C_4$) groups; $R^1$ and $R^2$ are, individually, methyl, ethyl, or methoxy radicals; AR is benzene or naphthalene; and when AR is benzene, m and n are, individually, integers from 0 to 5, inclusive, and x is an integer from 1 to 6, inclusive; when AR is naphthalene, m and n are, individually, integers from 0 to 3, inclusive, and x is an integer from 1 to 4, inclusive, which comprises:

1. reacting a secondary phosphine compound of the formula:

with at least a stoichiometric amount of formaldehyde to produce a dialkylhydroxymethylphosphine of the formula:

$(R)_2P - CH_2OH$ 2. reacting at least the stoichiometrically required amount of said dialkylhydroxymethylphosphine with a halomethyl aromatic compound of the formula:

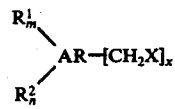

wherein X is a halogen atom, to produce a tertiary phosphine of the formula:

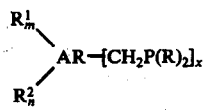

and
3. oxidizing said tertiary phosphine compound.

2. The method according to claim 1 wherein said oxidant is hydrogen peroxide.

3. The method according to claim 1 wherein AR is benzene, m is 3, n=0 and x is 1.

4. The method according to claim 1 wherein AR is benzene, m and n are each 0, and x is 2.

5. The method according to claim 1 wherein AR is benzene, $R^1$ and $R^2$ are methyl, m and n are each 2, and x is 2.

6. The method according to claim 1 wherein AR is benzene, $R^1$ and $R^2$ are each methyl, m is 3, n=0 and x is 3.

7. The method according to claim 1 wherein AR is benzene, $R^1$ and $R^2$ are each methyl, m and n are each 1, and x is 4.

8. The method according to claim 1 wherein AR is naphthalene, m and n are each 0, and x is 1.

9. The method according to claim 1 wherein AR is naphthalene, m and n are each 0, and x is 2.

10. The method according to claim 1 wherein AR is naphthalene, m and n are each 0, and x is 3.

11. The method according to claim 1 wherein AR is benzene, m and n are each 0, R is n-propyl, and x is 2.

12. The method according to claim 1 wherein AR is benzene, m and n are each 0, R is cyclohexyl, and x is 2.

* * * * *